(12) United States Patent
Zhou et al.

(10) Patent No.: US 10,405,738 B2
(45) Date of Patent: Sep. 10, 2019

(54) ELECTRONIC LARYNGOSCOPE

(71) Applicant: SHANGHAI ANQING MEDICAL INSTRUMENT CO., LTD, Shanghai (CN)

(72) Inventors: Zhenhua Zhou, Shanghai (CN); Zheng Yuan, Shanghai (CN)

(73) Assignee: SHANGHAI ANQING INSTRUMENT CO., LTD, Shanghai (CN)

(*) Notice: Subject to any disclaimer, the term of this patent is extended or adjusted under 35 U.S.C. 154(b) by 135 days.

(21) Appl. No.: 15/529,023

(22) PCT Filed: Jun. 24, 2015

(86) PCT No.: PCT/CN2015/082179
§ 371 (c)(1),
(2) Date: May 23, 2017

(87) PCT Pub. No.: WO2016/082540
PCT Pub. Date: Jun. 2, 2016

(65) Prior Publication Data
US 2017/0258312 A1 Sep. 14, 2017

(30) Foreign Application Priority Data
Nov. 24, 2014 (CN) .......................... 2014 1 0680629

(51) Int. Cl.
A61B 1/267 (2006.01)
A61B 1/00 (2006.01)
(Continued)

(52) U.S. Cl.
CPC .......... *A61B 1/267* (2013.01); *A61B 1/00009* (2013.01); *A61B 1/00094* (2013.01);
(Continued)

(58) Field of Classification Search
CPC ..... A61B 1/267; A61B 1/00094; A61B 1/015; A61M 2025/091
See application file for complete search history.

(56) References Cited

U.S. PATENT DOCUMENTS 5,363,838 A * 11/1994 George .............. A61B 1/00048
128/207.14
5,919,130 A * 7/1999 Monroe ................. A61B 1/227
600/129
(Continued)

FOREIGN PATENT DOCUMENTS

| CN | 201168310 A | 12/2008 |
| CN | 101920048 A | 12/2010 |

(Continued)

OTHER PUBLICATIONS

Machine translation of Description for CN204318710 Electronic laryngoscope, WIPO Patentscope, generated Jun. 1, 2018, 4 pages.*
(Continued)

*Primary Examiner* — Jacqueline T Johanas
(74) *Attorney, Agent, or Firm* — Knobbe Martens Olson & Bear LLP

(57) ABSTRACT

In some embodiments, an electronic laryngoscope includes a camera, a hollow connecting rod, a handle, and a control display. The front end of the connecting rod is connected to the camera, the rear end of the connecting rod is connected to the handle, and the rear end of the handle is connected to the control display. The laryngoscope further includes a hollow tube whose inner diameter is greater than the outer diameter of the connecting rod. The camera and the connecting rod are located on the inner side of the hollow tube. A sputum suction opening is formed between the front end of the hollow tube and the front end of the camera, and a sputum passage in communication with the opening is formed between the hollow tube and the connecting rod. The (Continued)

laryngoscope further includes a connector between the hollow tube and the camera and/or the connecting rod.

13 Claims, 6 Drawing Sheets

(51) Int. Cl.
    *A61B 1/012*     (2006.01)
    *A61B 1/05*     (2006.01)
    *A61B 1/015*     (2006.01)
    *A61M 25/09*     (2006.01)

(52) U.S. Cl.
    CPC ...... *A61B 1/00119* (2013.01); *A61B 1/00124* (2013.01); *A61B 1/012* (2013.01); *A61B 1/015* (2013.01); *A61B 1/053* (2013.01); *A61B 1/0014* (2013.01); *A61B 1/00112* (2013.01); *A61M 2025/091* (2013.01)

(56) References Cited

U.S. PATENT DOCUMENTS

| | | |
|---|---|---|
| 6,569,089 B1 | 5/2003 | Covington et al. |
| 7,922,650 B2* | 4/2011 | McWeeney ........ A61B 1/00071 |
| | | 600/104 |
| 7,946,981 B1* | 5/2011 | Cubb ................ A61B 1/00052 |
| | | 600/120 |
| 2005/0090712 A1 | 4/2005 | Cubb |
| 2010/0198012 A1* | 8/2010 | Poole ................ A61B 1/00096 |
| | | 600/115 |
| 2010/0204546 A1* | 8/2010 | Hassidov ........... A61B 1/00103 |
| | | 600/114 |
| 2011/0313347 A1 | 12/2011 | Zocca et al. |
| 2012/0059224 A1* | 3/2012 | Wellen ................ A61B 1/2275 |
| | | 600/200 |
| 2012/0259173 A1* | 10/2012 | Waldron ........... A61B 1/00073 |
| | | 600/109 |
| 2014/0107496 A1* | 4/2014 | Hellstrom .......... A61B 1/00135 |
| | | 600/478 |
| 2014/0276093 A1* | 9/2014 | Zeien ................. A61B 5/0077 |
| | | 600/476 |
| 2014/0288371 A1 | 9/2014 | Nakatate |
| 2015/0087906 A1* | 3/2015 | Kucklick .......... A61M 25/0662 |
| | | 600/114 |
| 2016/0058383 A1* | 3/2016 | Hellstrom ........... A61B 5/6852 |
| | | 600/430 |
| 2016/0345803 A1* | 12/2016 | Mallory ............ A61B 1/00068 |

FOREIGN PATENT DOCUMENTS

| | | |
|---|---|---|
| CN | 102307512 A | 1/2012 |
| CN | 203388832 U | 1/2014 |
| CN | 103906548 A | 7/2014 |
| CN | 204318710 U | 5/2015 |
| JP | 2005304650 A | 11/2005 |

OTHER PUBLICATIONS

Machine translation of Claims for CN204318710 Electronic laryngoscope, WIPO Patentscope, generated Jun. 1, 2018, 3 pages.*
International Search Report and Written Opinion dated Aug. 5, 2015 for International Application No. PCT/CN2015/082179, in 11 pages.

* cited by examiner

ELECTRONIC LARYNGOSCOPE

CROSS-REFERENCE TO RELATED APPLICATIONS

This application is a U.S. national phase of PCT/CN2015/082179, filed on Jun. 24, 2015, which claims the benefit of Chinese Patent Application No. 201410680629.5, filed on Nov. 24, 2014 and entitled "ELECTRONIC LARYNGOSCOPE," each of which is hereby incorporated by reference in its entirety.

TECHNICAL FIELD

The present invention relates to an electronic laryngoscope and in particular an electronic laryngoscope with a sputum suction apparatus.

BACKGROUND ART

An electronic laryngoscope is usually composed of a camera, a hollow hard tube (or "connecting rod"), a handle and a control display module. A camera is provided on the front end of the hollow hard tube and the rear end thereof is fixedly connected to the handle, and wires can be routed inside the hollow hard tube. The rear portion of the handle is connected to the control display module. In the process of diagnosis using the electronic laryngoscope, it is usually used with a tracheal hose (or "tracheal cannula", "tracheal catheter", "insert tube"), that is, inserting the hollow hard tube of the electronic laryngoscope into the tracheal hose, and the tracheal hose coating the hollow hard tube with a camera circumferentially goes deep into patients' laryngeal cavity.

In the process of diagnosis, the camera of the electronic laryngoscope will be completely covered by the sputum inside patients' laryngeal cavity, influencing physicians' checking effect. Therefore, the sputum needs to be removed in time. However, it's always been a difficulty in hospital work to use the electronic laryngoscope while suctioning the sputum or nursing laryngeal cavity of patients, especially patients in coma. That's because method of sputum suction applying conventional auxiliary instruments often cannot achieve the object to clear the sputum and dirt in mouth thoroughly and, meanwhile, it is also inconvenient to operate due to the complicated and overloaded auxiliary instruments.

Chinese utility model patent CN203388832 (a hose laryngoscope) has disclosed an improved way of sputum suction. In order to suction out the sputum, in this utility model patent, the sputum suction catheter is buried in the wall of the tracheal hose and axially extends along the tracheal hose. The rear end of the sputum suction catheter is provided with a sputum aspirator interface and the front end thereof has a small opening (that is "sputum suction opening") disposed on the inner wall of the front end part of the tracheal hose, and the sputum is suctioned out from the sputum suction opening through the sputum suction catheter.

Chinese utility model patent CN201168310 (a multifunctional light-emitting tracheal catheter) has also disclosed a solution of sputum suction, which has improvements similar to the utility model patent CN203388832. The sputum suction catheter is also buried in the wall of the tracheal hose, and the sputum suction opening is also a small opening which is disposed on the inner wall of the front end part of the tracheal hose.

In the above two utility model patents, the sputum suction catheter is buried in the wall of the tracheal hose, the defect of which is that the location of the sputum suction opening from the location of a camera cannot be determined. Under normal circumstances, the sputum suction opening would be in a position relatively far from the camera, for the specifications of the tracheal hose are relatively various and the sizes are different. According to the stipulations of the tracheal hose by Pharmaceutical industry standard YY0337.1-2002 of the People's Republic of China, there are 19 specifications on the tracheal hoses due to the difference of the inner diameter and the length matched with the inner diameter. Therefore, it is relative hard for the sputum suction opening disposed on the wall of the tracheal hose to match with or correspond to the location of the camera on the hollow hard tube, resulting in that the sputum or dirt around the camera cannot be removed or cleaned effectively.

Therefore, with respect to the prior art of the solution of sputum suction relative to the electronic laryngoscope, for the sputum suction openings are all far away from the camera or cannot be disposed stably around the camera and, meanwhile, the power of the sputum aspirator is relatively small (a relatively large sputum suction force would make patients feel uncomfortable, or injure their wall of laryngeal cavity), the sputum or dirt on the periphery of the camera cannot be removed effectively and completely. Even if the sputum suction opening happens to locate around the camera, the sputum around the camera cannot be removed effectively since the sputum suction can only be performed at a certain point on one side around the camera.

BRIEF DESCRIPTION OF THE INVENTION

The invention has the object to provide an electronic laryngoscope with a sputum suction apparatus, which can efficiently resolve the technical problem of the above prior art that the camera is sheltered by the sputum or dirt and has overcome the defects of the above prior art, so as to be capable of clearing the matter on the periphery of the camera rapidly and completely.

After a large number of experiments and research, the inventor of this invention found that forming a sputum suction opening and sputum suction passage in the area around the camera has better sputum suction effect and efficiency than suctioning the sputum at a certain point away from the camera, and it is more convenient and more beneficial to the medical staff to use the integrative operating mode. The invention is fulfilled based on the above findings.

The invention provides an electronic laryngoscope, comprising: a camera module with a camera, a hollow connecting rod, a handle and a control display module; wherein, the front end of the connecting rod is connected to the camera module, the rear end of the connecting rod is connected to the handle, and the rear end portion of the handle is connected to the control display module. The electronic laryngoscope further comprises a hollow tube whose inner diameter is greater than the outer diameter of the connecting rod. The camera module and the connecting rod are located on the inner side of the hollow tube. A sputum suction opening is formed between the front end of the hollow tube and the front end of the camera module, and a sputum passage communicating with the sputum suction opening is formed between the hollow tube and the connecting rod; connecting apparatuses connecting the hollow tube with the camera module and/or the connecting rod.

Preferably, the connection of the connecting apparatus is a detachable connection.

Further, the number of the connecting apparatus is more than one, and the connecting apparatuses with the same or different structures can be set simultaneously.

Preferably, the connecting apparatus includes an engagement structures disposed on the front end portions of both the camera module and the hollow tube, and a sputum suction opening is formed among the parts in which there are no the engagement structures on the front end portions of both the camera module and the hollow tube.

Further, the engagement structure comprises: more than one recesses axially downward disposed on the wall of the front end portion of the hollow tube; projections disposed circumferentially on the front end portion of the camera module, corresponding one-to-one to the shape of each recess respectively, and capable of engaging therewith. The connecting apparatus connects the hollow tube with the camera module and/or the connecting rod fixedly by the projections inserting into the recesses and engaging with each other.

Further, the recesses are a pair of recesses symmetrical with the tube axis of the hollow tube as the center.

Further, after the projections engage with the recesses, the transition between the outer peripheral surface of the projections and the outer peripheral surface of the hollow tube is continuous and smooth.

Preferably, the sputum suction mouth is an annular structure which is the front end of the part in which the front end wall of the hollow tube surrounds the camera module. The front end wall of the hollow tube is at a certain distance from the camera module, and an annular space is formed therebetween.

Further, the connecting apparatus further comprises: screws or detachable fixing pins; at least one screw holes or pin holes disposed on the peripheral surface of the rear end portion of the camera module or/and the peripheral surface of the connecting rod; through-holes corresponding to the screw holes or pin holes disposed on the wall of the hollow tube. The connecting apparatus connects the hollow tube with the camera module and/or the connecting rod by screwing the screws with the screw holes through the through-holes, or by inserting the fixing pins into the pin holes through the through-holes and the fixing connection.

Preferably, the hollow tube and the connecting rod extend and connect to the inside of the handle simultaneously. A sputum aspirator interface communicating with the sputum passage of the hollow tube is disposed around the handle, or around the part of the hollow tube located outside of the oral cavity of patient when using the electronic laryngoscope so that the sputum suctioned through the sputum suction opening can flow out of the sputum aspirator interface through the sputum passage.

Further, the material of the hollow tube is hard and bendable material, and the material of the connecting rod is hard and bendable material or soft material.

Further, a drug delivery catheter can be disposed in the sputum passage of the hollow tube. The camera is located on the central part of the camera module corresponding to the tube axis of the hollow tube, and a lighting module and/or drug injection hole communicating with the drug delivery catheter is disposed on the peripheral areas of the camera module surrounding the camera are provided with. The drug injection hole facilitates guiding the drugs injected from the handle through the drug delivery catheter into the patient's body.

Preferably, the electronic laryngoscope of the invention further comprises a sputum suction catheter located outside of the hollow tube and the connecting rod. The hollow tube at least surrounds the camera module, and an enclosed connection structure is formed between the rear end of the hollow tube and the rear end of the camera module or the connecting rod, which is forming a rear enclosed end. The rear enclosed end is provided with a sputum guide hole through which the sputum passage of the hollow tube communicates with the sputum suction catheter.

Further, the rear enclosed end is also provided with a drug injection hole. The drug delivery catheter communicates with the sputum passage of the hollow tube through the drug injection hole, or the drug delivery catheter penetrates through the drug injection hole and extends to the areas around the camera module.

Preferably, the electronic laryngoscope of the invention further comprises a sputum suction catheter located outside the hollow tube and the connecting rod; the hollow tube at least surrounds the front end portion of the camera module, and an enclosed connection structure is formed between the front end of the hollow tube and the front end of the camera module, which is forming a front enclosed end; wherein, an outer end surface of the front enclosed end is provided with an annular sputum guide groove surrounding the camera module, the bottom of the sputum guide groove is provided with a hole-shaped sputum suction opening, and the sputum suction catheter penetrates through the rear end of the hollow tube to communicate with the sputum suction opening.

Further, the sputum guide groove can completely, partly or not border to the camera module; the annular structure of the sputum guide groove can be closed or open.

Furthermore, the outer end surface of the front enclosed end is further provided with a drug injection hole, and the drug delivery catheter penetrates through the rear end of the hollow tube to communicate with the drug injection hole.

According to the electronic laryngoscope of the present invention, the sputum and dirt on the periphery of the camera can be cleared rapidly, effectively and thoroughly; and the product has a simple structure and the integrative function of camera shooting, sputum suction, lighting and drug dosing, and it is more convenient and more beneficial for the medical stuff to use the operating mode.

DESCRIPTION OF REFERENCE NUMBER

Figure 1:
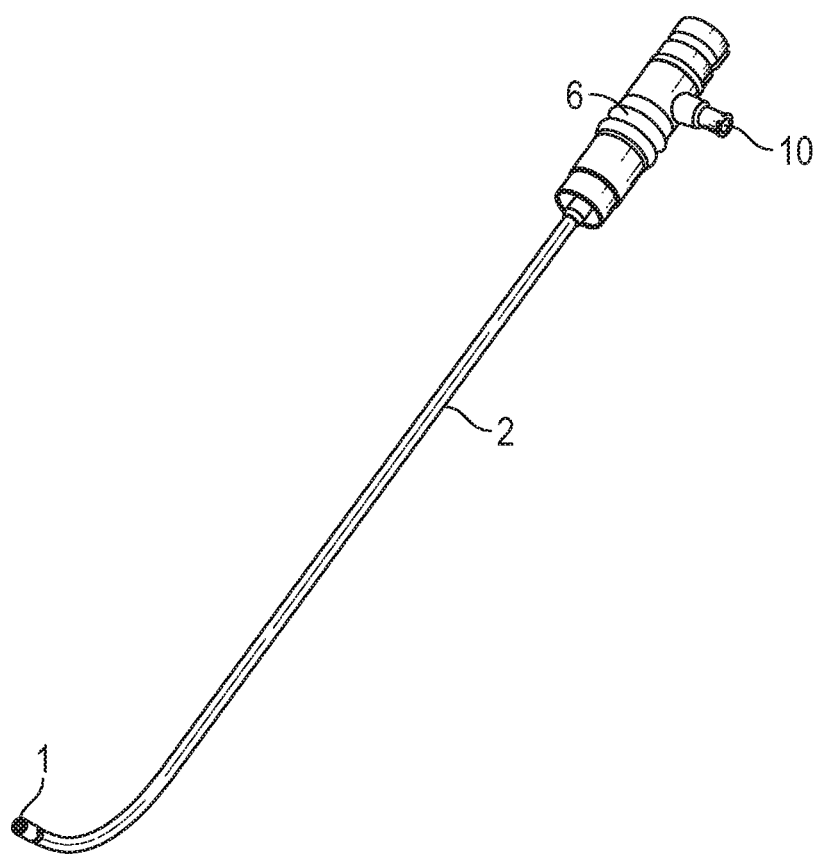
FIG. 1 is a schematic view showing the overall structure of an embodiment of the present invention.

1. Camera module
2. Hollow tube
3. Connecting rod
4. Sputum passage
5. Sputum suction opening
6. Handle
7. Projection
8. Recess
9. Fixing pin
10. Sputum aspirator interface
11. Lighting module
12. Sputum suction catheter
13. Sputum guide groove
14. Rear enclosed end
15. Front enclosed end

DETAILED DESCRIPTION OF THE INVENTION

In connection with the Drawing, preferred embodiments of the present invention are described specifically as follows, Embodiment 1

An electronic laryngoscope of the present invention is shown in FIGS. 1-4. The present embodiment has a basic structure of a traditional electronic laryngoscope, as a whole comprising: a camera module 1 with a camera, a hollow connecting rod 3, a handle 6, and a control display module (not shown);

wherein, the front end of the connecting rod 3 is connected to the camera module 1, the rear end of the connecting rod 3 is connected to the handle 6, and the rear end of the handle 6 is further connected to the control display module; and the inside of the rod of the connecting rod 3 is provided with wires to communicate the camera module 1 with the control display module.

Figure 2:
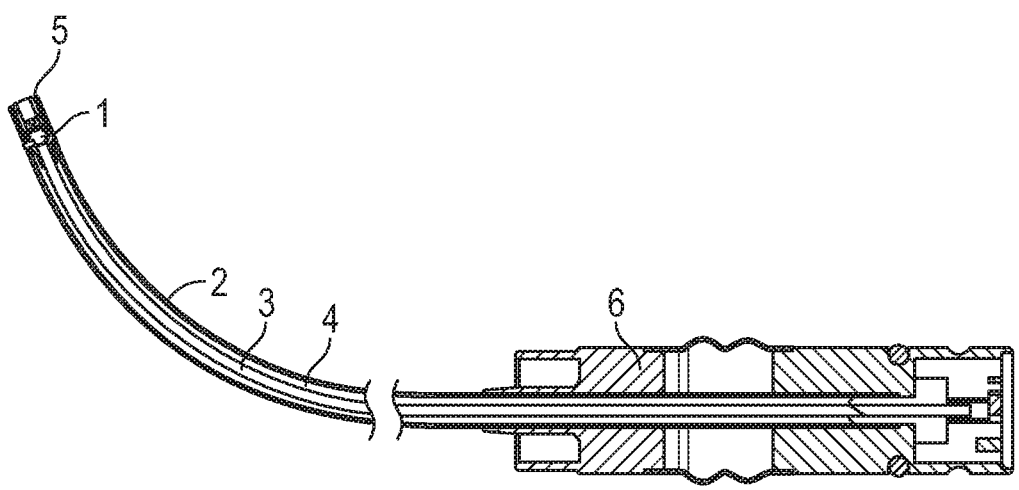
FIG. 2 is a sectional view of the embodiment in FIG. 1.

Unlike the prior art, the electronic laryngoscope of the present embodiment further comprises: a hollow tube 2 whose inner diameter is greater than the outer diameter of the connecting rod 3, the size of inner diameter of the hollow tube 2 ranging from 0.5 millimeter to 10 millimeters and the size of the thickness of wall of the hollow tube 2 ranging from 0.1 millimeter to 2 millimeters; wherein as shown in FIG. 2, the camera module 1 and the connecting rod 3 are located on the inner side of the hollow tube 2, a sputum suction opening 5 is formed between the front end of the hollow tube 2 and the front end of the camera module 1, and a sputum passage 4 communicating with the sputum suction opening 5 is formed between the hollow tube 2 and the connecting rod 3.

The electronic laryngoscope of the present embodiment further comprises a connecting apparatus connecting the hollow tube 2 and the camera module 1.

Figure 3:
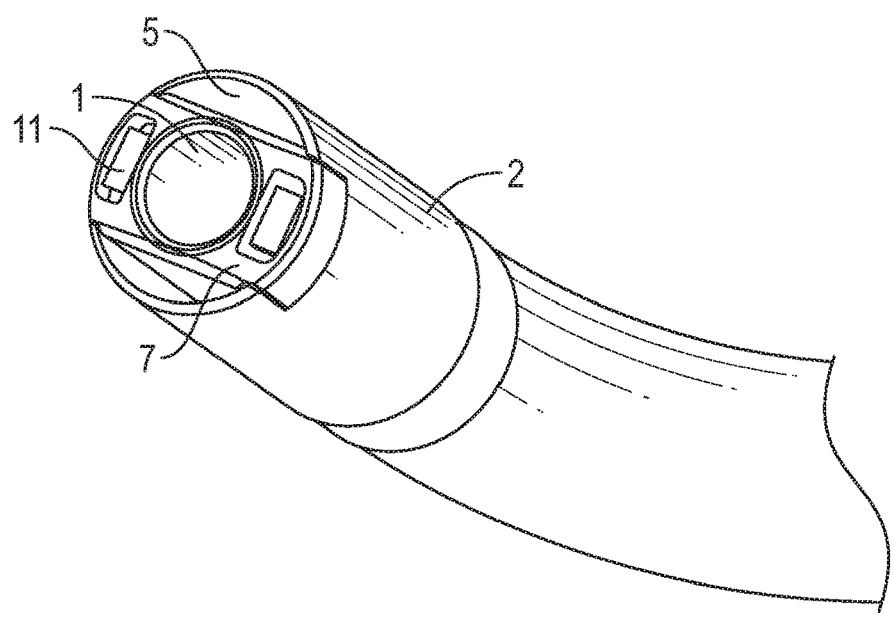
FIG. 3 is a schematic view showing the structure of a connecting apparatus of an embodiment of the invention.
Figure 4:
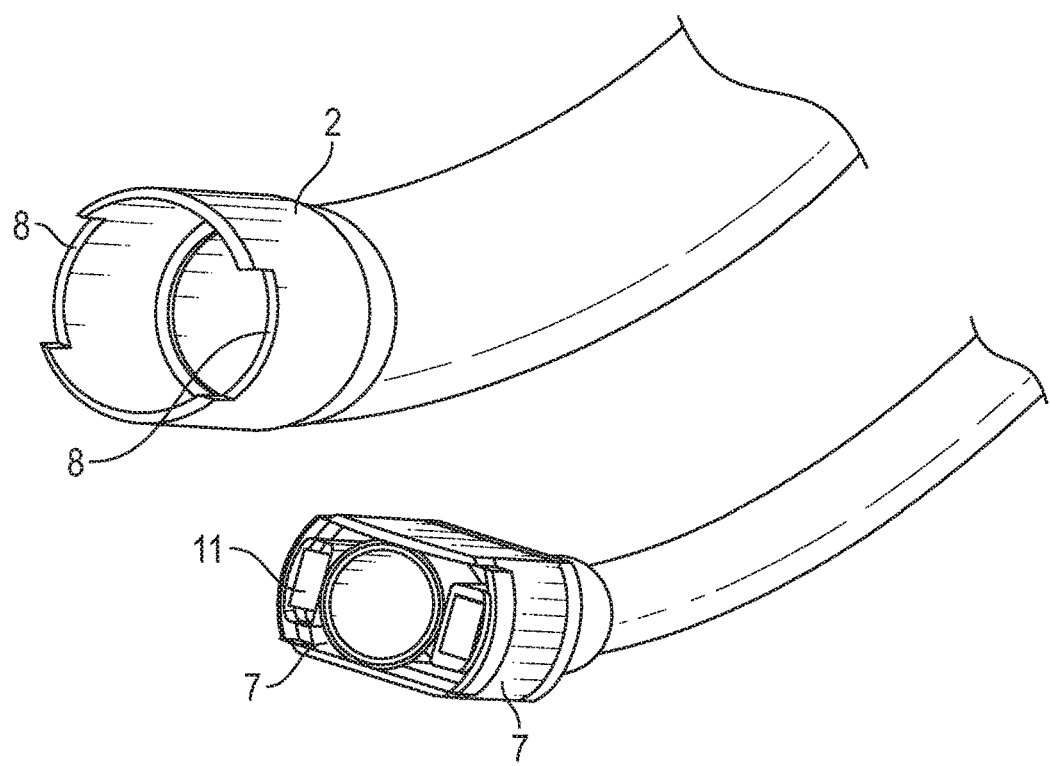
FIG. 4 is an exploded view of the embodiment in FIG. 3.

As shown in FIGS. 3 and 4, the connecting apparatus is engagement structures disposed on the front end portions of both the camera module 1 and the hollow tube 2, and a sputum suction opening 5 is formed among the parts in which there are no engagement structures on the front end portions of both the camera module 1 and the hollow tube 2 which is not disposed the engagement structure.

The engagement structure comprises: recesses 8 axially downward disposed on the wall of the front end portion of the hollow tube 2; projections 7 disposed circumferentially on the front end portion of the camera module 1 and corresponding one-to-one to recesses 8 in shape and capable of engaging therewith; the connecting apparatus connects the hollow tube 2 with the camera module 1 by the projections 7 inserting into the recesses 8 and clamping with each other.

In the present embodiment, the recesses 8 are a pair of recesses 8 symmetrical with the tube axis of the hollow tube 2 as the center; correspondingly, the projections 7 are a pair of projections 7 symmetrical with the tube axis of the hollow tube 2 as the center, disposed on both sides of the front end portion of the camera module 1. In the engagement structures, as shown in FIG. 3, the front ends of the camera module 1, the projections 7, and the hollow tube 2 form two semiarc-shaped sputum suction openings 5 separated by the camera module 1 and the projections 7.

In the present embodiment, the front end faces of the sputum suction openings 5 and the camera module 1 is at the same level, that is, the front end face of the hollow tube 2 and the front end face of the camera module 1 is at the same level. Optionally, the front end face of the hollow tube 2 can be higher or lower than the front end face of the camera module 1.

Further, as shown in FIG. 3, after the engagement of the projections 7 and the recesses 8, the transition of the outer peripheral face of the projections 7 and the outer peripherals face of the hollow tube 2 is continuous and smooth.

In the present embodiment, the front end face of the projections 7 is flat, and a lighting module 11 can be inserted thereon. Optionally, on the front end face of the projections 7 in close proximity to the camera module 1, a sputum guide groove (not shown) can be set to guide the sputum on the projections 7 to the sputum suction opening 5.

Optionally, the number of the recesses 8 and the number of the corresponding projections 7 can be one or multiple; the shape of the recesses 8 is not limited to be rectangle in the present embodiment but can be any other shapes suitable for engagement; in the case of multiple recesses 8, the shapes or sizes of recesses 8 can be the same or different.

Optionally, the engagement of the recesses 8 and the projections 7 is not limited to the insertion type in the present embodiment but can be embedded type; that is, the recesses 8 are dented hole or dented pits disposed on the wall of the front end portion of the hollow tube 2, at the meantime, the corresponding projections 7 are disposed circumferentially on the front end portion of the camera module 1, and the projections 7 can be embedded in the recesses 8; in the case of embedded-type engagement, the location of the projections 7 and the recesses 8 can be disposed reversely, that is, the recesses 8 are dented pits disposed circumferentially on the front end portion of the camera module 1, at the meantime, the corresponding projections 7 are disposed on the inner wall of the front end portion of the hollow tube 2.

As shown in FIGS. 1 and 2, the hollow tube 2 and the connecting rod 3 extend and connect to the inside of the handle 6 simultaneously; the peripheral surface of the handle 6 is provided with a sputum aspirator interface 10 communicating with the sputum passage 4 of the hollow tube 2 so that the sputum suctioned through the sputum suction opening 5 can flow out of the sputum aspirator interface 10 through the sputum passage 4. Optionally, when using the electronic laryngoscope, the sputum aspirator interface 10 can also be disposed on the peripheral surface of the hollow tube 2 located outside of the oral cavity of patients.

If the material of the hollow tube 2 is hard and bendable material, the material of the connecting rod 3 can be soft material, not necessarily the traditional metallic hard material.

If the material of the connecting rod 3 is hard material, the material of the hollow tube 2 can be soft material, and meanwhile the hard material can be chosen to be applied to the part of hollow tube 2 covering the camera module 1 can choose.

Further, a drug delivery catheter (not shown) can be disposed in the sputum passage 4 of the hollow tube 2; the camera is located on the central part of the camera module 1 corresponding to the tube axis of the hollow tube 2, the peripheral areas of the camera module 1 surrounding the camera are provided with a lighting module 11 and/or drug injection holes (not shown) communicating with the drug delivery catheter; the drug injection holes facilitates guiding the drugs injected from the handle 6 through the drug delivery catheter into the patient's body.

Embodiment 2

Figure 5:
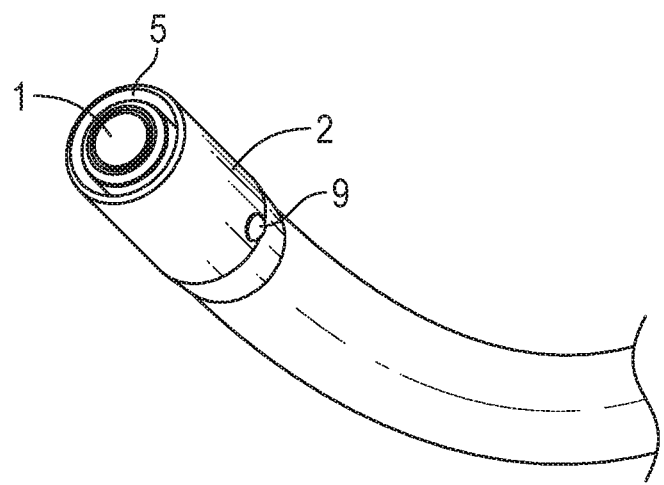
FIG. 5 is a schematic view showing the structure of a connecting apparatus in an embodiment of the present invention.
Figure 6:
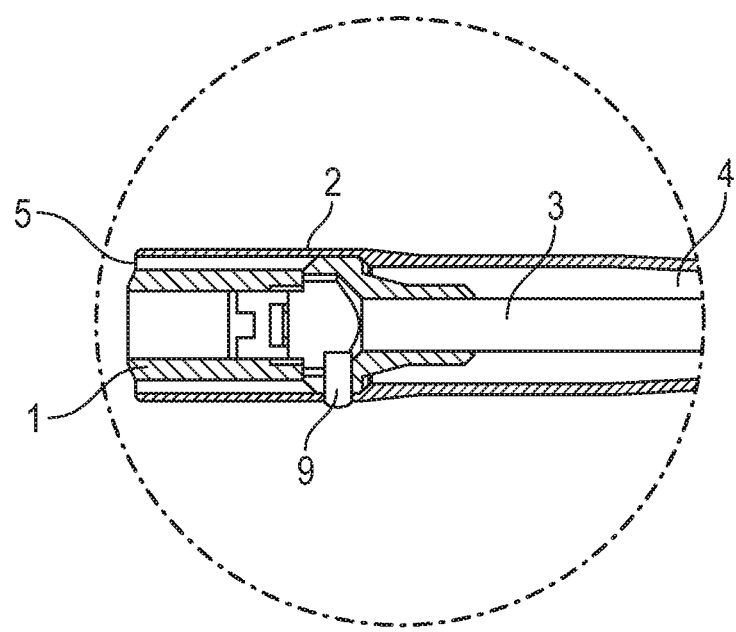
FIG. 6 is a sectional view of the embodiment in FIG. 5.

An electronic laryngoscope with another sputum suction opening shape and connecting apparatus is shown in FIGS. 5 and 6, and the structure of other parts is basically the same as that in embodiment 1.

The sputum suction opening 5 in the present embodiment is a annular structure; the annular structure is a front end of the part in which the front end wall of the hollow tube 2 surrounds the camera module 1, the front end wall of the hollow tube 2 remains a certain distance from the camera module 1, and an annular space is formed therebetween.

The connecting apparatus of the present embodiment is detachable fixing pins 9, the peripheral surface of the rear end portion of the camera module 1 is provided with pin holes, the wall of the hollow tube 2 is provided with through-holes corresponding to the pin hole, the hollow tube 2 and the camera module 1 can be fixed connected by inserting the fixing pins 9 into the pin holes through the through-holes.

The number of the fixing pins 9 is more than one, preferably a pair of fixing pins symmetrical with the tube axis of the hollow tube 2 as the center.

Optionally, the peripheral surface of the connecting rod 3 can be provided with at least one pin holes so as to fixedly connect the hollow tube 2 and the camera module 1 by the fixing pins.

Optionally, the connecting apparatus can also be more than one screws, the peripheral surface of the rear end portion of the camera module 1 or/and the peripheral surface of the connecting rod 3 are provided with at least one screw holes, the wall of the hollow tube 2 is provided with through-holes corresponding to the screw holes, the hollow tube 2 and the camera module 1 and/or the connecting rod 3 can be fixedly connected by screwing the screw with the screw holes through the through-holes.

Optionally, the number of the connecting apparatus is more than one, and the connecting apparatuses with the same or different structures can be disposed in one electronic laryngoscope simultaneously. For example, the connecting apparatuses in the form of screws and fixing pins can be provided simultaneously, and the connecting apparatus in the form of the engagement structures and screws or fixing pins can also be provided simultaneously, and so on.

It is to be noted, the structure of the connecting apparatus should not be limited to the preferred case of the present embodiment, but also comprise other implementable connecting structures capable of fixedly connect the hollow tube 2 with the camera module 1 and/or connecting rod 3, such as hook connection, spline connection and threaded connection et al.

Embodiment 3

Figure 7:
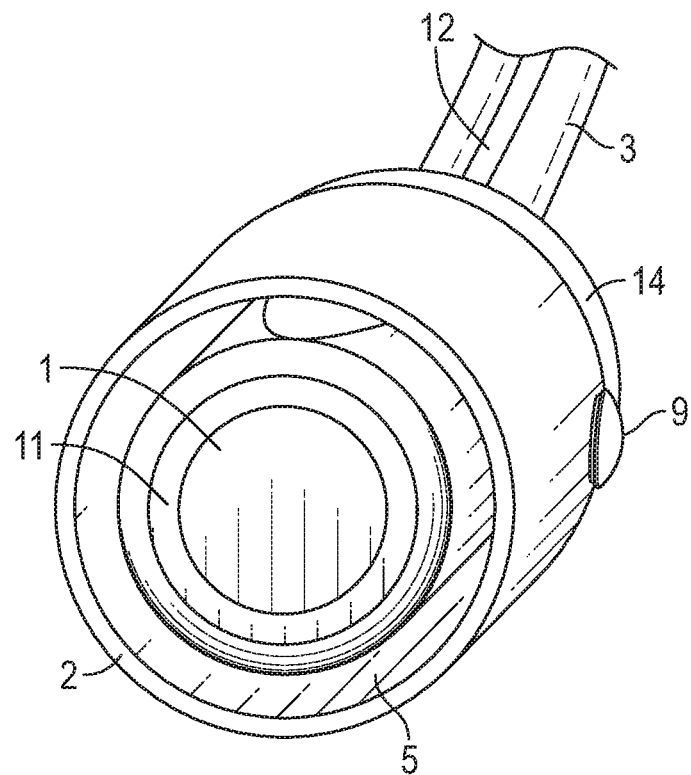
FIG. 7 is a partial structural schematic view of an embodiment of the present invention.
Figure 8:
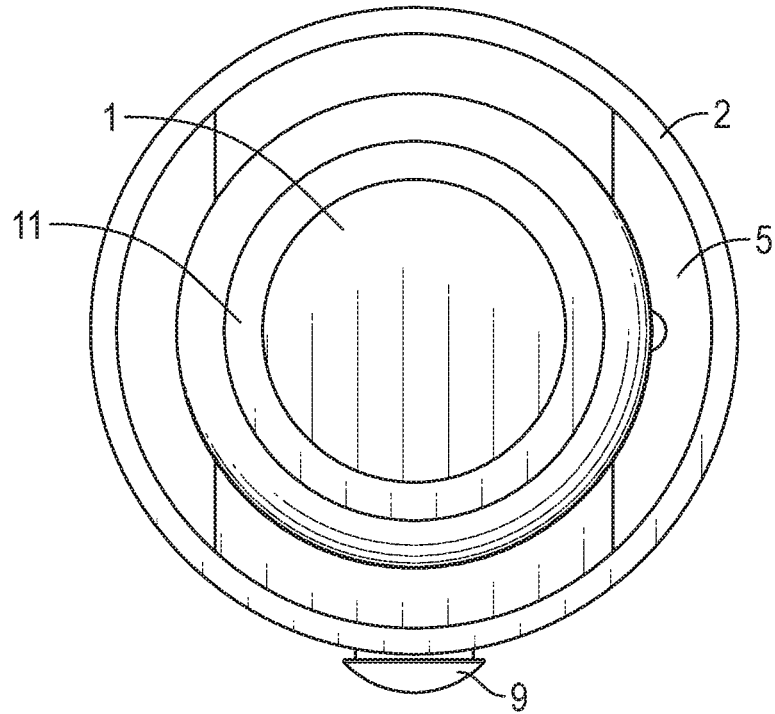
FIG. 8 is the front view of the embodiment in FIG. 7 along the direction when the top end of the camera module faces downward.
Figure 9:
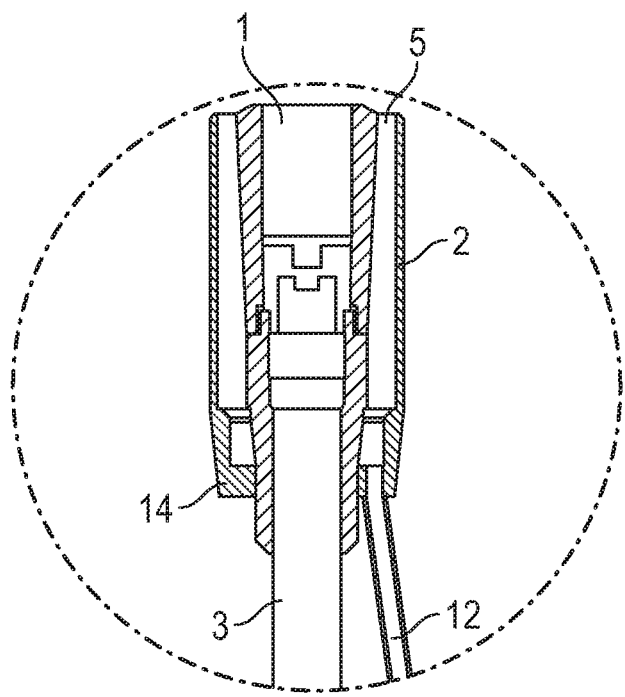
FIG. 9 is a sectional view of the embodiment in FIG. 7.

An electronic laryngoscope in which the hollow tube does not extend fully to the inside of the handle is shown in FIGS. 7-9.

In the present embodiment, the electronic laryngoscope further comprises a sputum suction catheter 12 located outside of the hollow tube 2 and the connecting rod 3; the hollow tube 2 surrounds the camera module 1, an enclosed connection structure is formed between the rear end of the hollow tube 2 and the rear end of the camera module 1, forming a rear enclosed end 14; the rear enclosed end 14 is provided with a sputum guide hole through which the sputum passage 4 of the hollow tube 2 communicates with the sputum suction catheter 12.

In the present embodiment, the periphery of the handle 6 or the hollow tube 2 is not provided with a sputum aspirator interface 10, instead, employing the sputum suction catheter in prior art, which means that the rear end of the sputum suction catheter is connected with a sputum aspirator interface.

The sputum suction opening 5 in this embodiment is annular in shape, and the structure of the connecting apparatus is in the form of fixing pins.

Optionally, the structure and choice of the connecting apparatus in the present embodiment can be the same as that in embodiments 1 and 2.

Or, only the rear enclosed end 14 is provided as the connecting apparatus. The structure of the connecting apparatus comprises, but is not limited to, interference connection or threaded connection et al. Taking the interference connection as an example, the rear enclosed end 14 of the hollow tube 2 is connected with the parts around the rear end portion of the camera module 1 or the connecting rod 3 by directly capping thereon. Taking the threaded connection as another example, threads are disposed on the peripheral face of the rear end portion of the camera module 1 or the outer peripheral face of the connecting rod 3, with the rear enclosed end 14 having a certain thickness from front to rear, corresponding threads are disposed on the inner peripheral face of the rear enclosed end 14, and the camera module 1 or the connecting rod 3 can be screwed with the rear enclosed end 14.

Optionally, on the rear enclosed end 14, there is also provided an drug injection hole (not shown). The drug delivery catheter (not shown) communicates with the sputum passage 4 of the hollow tube 2 through the drug injection hole, or the drug delivery catheter penetrates through the drug injection hole and extends to the periphery of the camera module 1.

Embodiment 4

Figure 10:
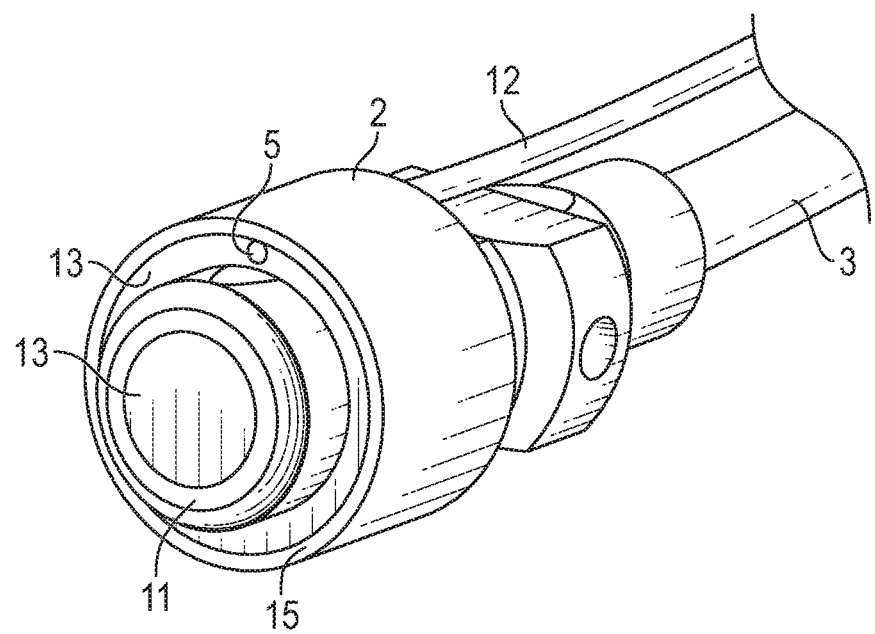
FIG. 10 is a partial structural schematic view of an embodiment of the present invention.
Figure 11:
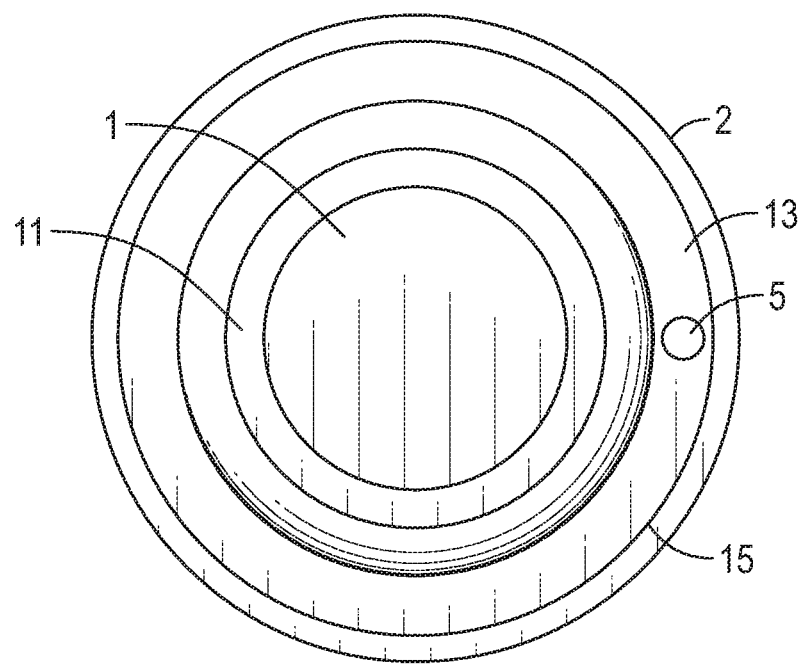
FIG. 11 is the front view of the embodiment in FIG. 10 along the direction when the top of the camera module faces downward.
Figure 12:
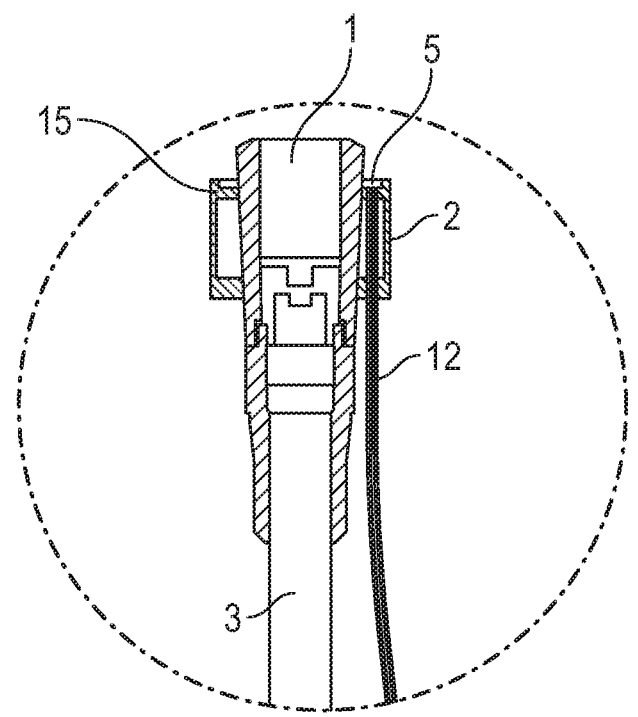
FIG. 12 is a sectional view of the embodiment in FIG. 10.

An electronic laryngoscope with a sputum guide groove is shown in FIGS. 10-12.

In the present embodiment, the electronic laryngoscope further comprises a sputum suction catheter 12 located outside of the connecting rod 3, and most part of the sputum suction catheter 12 with the tube head part in the front end thereof penetrating into the hollow tube 2 is located outside of the hollow tube 2; the hollow tube 2 at least surrounds the front end portion of the camera module 1, an enclosed connection structure is formed between the front end of the hollow tube 2 and the front end of the camera module 1, forming a front enclosed end 15; wherein, on the outer end surface of the front enclosed end 15, there is provided an annular sputum guide groove 13 surrounding the camera module 1, on the bottom of the sputum guide groove 13, there is provided a hole-shaped sputum suction opening 5, and the sputum suction catheter 12 penetrates through the rear end of the hollow tube 2 to communicate with the sputum suction opening 5.

Optionally, the groove depth of the sputum guide groove 13 is progressively deeper with approaching the area near the sputum suction opening 5; the sputum guide groove 13 can completely, partly or not border to the camera module 1; the annular structure of the sputum inducement groove 13 can be closed or open, preferably be closed in the present embodiment.

The connecting structures of the hollow tube 2 with the camera module 1 or the connecting rod 3 comprise the above connecting apparatuses, which can all be disposed on the rear of the front enclosed end 15. The connecting structure of the present embodiment is an interference connection, that is, the front enclosed end 15 of the hollow tube 2 is connecting to the periphery of the front end portion of the camera module 1 by directly capping thereon, not any other connecting apparatus provided.

Optionally, the threaded connection can also be individually employed. Threads are provided on the peripheral face of the front end portion of the camera module 1, with the front enclosed end 15 having a certain thickness from front to rear, and corresponding threads are provided on the inner side face of the front enclosed end 15, and the camera module 1 can be screwed with the front enclosed end 15.

Optionally, the sputum passage 4 is not provided between the hollow tube 2 and the camera module 1 or the connecting rod 3, and the sputum suction catheter 12 penetrates through the rear end of the hollow tube 2 to communicate with the sputum suction opening 5.

Optionally, on the outer end surface of the front enclosed end 15 there is also provided a drug injection hole (not shown). The drug delivery catheter (not shown) penetrates through the rear end of the hollow tube 2 to communicate with the drug injection hole.

Optionally, the material of the hollow tube 2 can be plastic or rubber.

The embodiments of the specific implementation way in the present invention are described above, and the description intends to clearly describe the inventive concept of the present invention but not limit the scope of the present invention as defined in the claims. According to the inventive concept of the present invention, the skilled in the art can easily make variations and modifications on the above embodiments, and the variations and modifications of the present invention are all included within the scope of protection of the present invention as defined in the appended claims.

The invention claimed is:

1. An electronic laryngoscope, comprising:
 a camera, a hollow connecting rod, and a handle, wherein a front end portion of said hollow connecting rod is connected to said camera, a rear end portion of said hollow connecting rod is connected to said handle;
 a hollow tube wherein an inner diameter of the hollow tube is greater than an outer diameter of said hollow connecting rod, wherein said camera and said hollow connecting rod are located on an inner side of said hollow tube;
 a sputum suction opening is formed between a front end portion of said hollow tube and a front end portion of said camera;
 a sputum passage communicating with said sputum suction opening, the sputum passage formed between said hollow tube and said hollow connecting rod; and
 a connector connecting said hollow tube to said camera and/or said hollow connecting rod, wherein said sputum suction opening includes an annular structure.

2. The electronic laryngoscope as claimed in claim 1, wherein a connection of said connector is detachable.

3. The electronic laryngoscope as claimed in claim 2, wherein the connector includes an engagement disposed on the front end portions of both said camera and said hollow tube, and wherein the sputum suction opening is positioned where there is no engagement on the front end portions of both said camera and said hollow tube.

4. The electronic laryngoscope as claimed in claim 3, wherein said engagement comprises:
 two or more recesses disposed axially downward on a wall of the front end portion of said hollow tube; and
 projections disposed circumferentially on the front end portion of said camera, wherein the shape of each projection correspond to a shape of the corresponding recess and the projections are configured to engage with the recesses;
 wherein said connector is configured to connect said hollow tube to said camera and/or said hollow connecting rod by inserting said projections into said recesses and clamping the projections with the recesses.

5. The electronic laryngoscope as claimed in claim 4, wherein said recesses include a pair of recesses symmetrical with a tube axis of said hollow tube as the center.

6. The electronic laryngoscope as claimed in claim 5, wherein after said projections engage with said recesses, a transition from an outer peripheral face of said projections to an outer peripheral face of said hollow tube is continuous and smooth.

7. The electronic laryngoscope as claimed in claim 1, wherein said connector comprises:
 screws or detachable fixing pins, wherein at least one of screw or pin holes is disposed on a peripheral face of the rear end portion of said camera or/and a peripheral face of said hollow connecting rod; and
 through-holes corresponding to said screw holes or pin holes on a wall of said hollow tube;
 wherein said connector connects said hollow tube to said camera and/or the hollow connecting rod by screwing said screws with said screw holes through said through-holes or by inserting said detachable fixing pins into said pin holes through said through-holes.

8. The electronic laryngoscope as claimed in claim 1, further comprising a sputum aspirator interface around said handle or around a portion of said hollow tube located outside of an oral cavity of a patient when using said electronic laryngoscope, the sputum aspirator interface communicating with the sputum passage of said hollow tube such that a sputum suctioned through the sputum suction opening flows out of said sputum aspirator interface through said sputum passage, and wherein said hollow tube and said hollow connecting rod is configured to extend and connect to the inside of said handle simultaneously.

9. The electronic laryngoscope as claimed in claim 8, wherein said hollow tube comprises a hard and bendable material, and said hollow connecting rod comprises a hard and bendable material or soft material.

10. The electronic laryngoscope of claim 8, further comprising:
   a lighting module disposed on peripheral areas of a camera module and surrounding said camera,
   wherein said camera is located on a central part of said camera module corresponding to a tube axis of said hollow tube.

11. The electronic laryngoscope as claimed in claim 1, further comprising a sputum suction catheter located outside of said hollow tube and said hollow connecting rod;
   wherein said hollow tube surrounds at least said camera;
   wherein an enclosed connection structure is formed between a rear end portion of said hollow tube and the rear end portion of said camera, forming a rear enclosed end portion;
   wherein said rear enclosed end portion includes a sputum guide hole through which the sputum passage of said hollow tube communicates with said sputum suction catheter.

12. The electronic laryngoscope as claimed in claim 1, further comprising:
   a sputum suction catheter disposed outside of said hollow tube and said hollow connecting rod, wherein said hollow tube at least surrounds the front end portion of said camera;
   an enclosed connector disposed between a front end portion of said hollow tube and the front end portion of said camera, forming a front enclosed end portion;
   an annular sputum inducement groove surrounding the camera on an outer end surface of said front enclosed end portion; and
   a hole-shaped sputum suction opening disposed on a bottom of the annular sputum inducement groove, wherein said sputum suction catheter is configured to penetrate through the rear end portion of said hollow tube to communicate with said sputum suction opening.

13. The electronic laryngoscope as claimed in claim 12, wherein said annular sputum inducement groove is positioned at least partly deeper in the front enclosed end portion than said camera.

* * * * *